United States Patent
Imran

(10) Patent No.: US 8,628,959 B2
(45) Date of Patent: Jan. 14, 2014

(54) METHODS FOR CANCER TREATMENT USING STEM CELLS

(75) Inventor: Mir Imran, Los Altos Hills, CA (US)

(73) Assignee: Incube Labs, LLC, San Jose, CA (US)

( * ) Notice: Subject to any disclaimer, the term of this patent is extended or adjusted under 35 U.S.C. 154(b) by 440 days.

(21) Appl. No.: 12/800,925

(22) Filed: May 24, 2010

(65) Prior Publication Data

US 2011/0002964 A1 Jan. 6, 2011

Related U.S. Application Data

(60) Provisional application No. 61/217,013, filed on May 23, 2009, provisional application No. 61/336,012, filed on Jan. 13, 2010.

(51) Int. Cl.
| | |
|---|---|
| *C12N 5/071* | (2010.01) |
| *C12N 5/074* | (2010.01) |
| *C12N 5/0787* | (2010.01) |
| *C12N 5/09* | (2010.01) |
| *C12N 5/16* | (2006.01) |

(52) U.S. Cl.
USPC ........... 435/373; 435/374; 435/377; 435/70.3

(58) Field of Classification Search
None
See application file for complete search history.

(56) References Cited

FOREIGN PATENT DOCUMENTS

| WO | WO03/016507 | * | 2/2003 |
|---|---|---|---|
| WO | WO03/086373 | * | 10/2003 |
| WO | WO2005/003320 | * | 1/2005 |

OTHER PUBLICATIONS

Kolf et al, Arthritis Research and Therapy, 2007, vol. 9, pp. 1-10.*
Dirks (Journal of Clinical Oncology, 2008, vol. 26, pp. 2916-2924).*
Ferrand, et al., "Human Bone Marrow-Derived Stem Cells Acquire Epithelial Characteristics through Fusion with Gastrointestinal Epitjelial Cells" *PloS ONE*, May 2011, vol. 6 issue 5, e19569, pp. 1-11.

* cited by examiner

*Primary Examiner* — Karen Canella
(74) *Attorney, Agent, or Firm* — Alston & Bird LLP

(57) ABSTRACT

Various embodiments of the invention provide methods of treating cancer. Many embodiments provide methods of treating cancer using stem cells. In one embodiment the method comprises removing cancer cells from a patient and culturing the cancer cells in the presence of stem cells under conditions such that the stem cells differentiate into stem cell-derived cancer cells (SCDCC) which can comprise stem cell derived non-invasive and/or invasive cancer cells. An amount of the SCDCC is introduced into the patient sufficient to induce the patient's immune system to produce antibodies which inhibit or destroy the patient's cancer cells. The SCDCC may also be genetically modified to produce various immune stimulating proteins which enhance the patient's immune response to the cancer cells and improves the efficacy of the SCDNIC in treating the patient's cancer.

19 Claims, No Drawings

METHODS FOR CANCER TREATMENT USING STEM CELLS

RELATED APPLICATIONS

This application claims the benefit of priority to Provisional U.S. Patent Application No. 61/217,013, entitled "METHOD FOR CANCER TREATMENT USING EMBRYONIC STEM CELLS", filed May 23, 2009; the aforementioned priority application being hereby incorporated by reference for all purposes.

This application also claims the benefit of priority to Provisional U.S. Patent Application No. 61/336,012, entitled "METHOD FOR CANCER TREATMENT USING STEM CELLS", filed Jan. 13, 2010; the aforementioned priority application being hereby incorporated by reference for all purposes.

FIELD OF THE INVENTION

Embodiments of the invention relate to the use of stem cells for the treatment of cancer.

BACKGROUND OF THE INVENTION

People of all ages may be affected with cancer, with the risk generally increasing with age. About 13% of all human deaths are caused by cancer so it is a significant health problem. Cancer is usually treated with a combination of surgery, chemotherapy and radiotherapy. In spite of advances in treatment, there still remains a need for more efficacious treatment regimens for cancer.

In the past 15 years, many discoveries have been made in understanding stem cells. There have been proposals to use stem cells for treating a wide variety of afflictions, including Parkinson's disease, spinal cord injuries, amyotrophic lateral sclerosis, and multiple sclerosis. Described herein are novel methods for the use of stem cells for the treatment of cancer.

SUMMARY OF THE INVENTION

Embodiments of the invention provide methods for treating cancer. Various embodiments provide methods for the treatment of cancer using stem cells. Many embodiments involve the use of stem cells which are induced to differentiate into mimics of a patient's cancers cells (e.g., antigen presentation), such that an immune response is developed against the cancer cells. The stem cells can be co-cultured with cancers cells removed from the patient to induce the stem cells to differentiate in order to mimic one or more antigens or other aspects of the cancers cells and then these cancer cell mimics are introduced into the patient's body to evoke an immune response against the cancer cells. In one embodiment, the method comprises removing cancer cells from a patient and culturing the cancer cells in the presence of embryonic or other stem cells under conditions such that the embryonic or other stem cells differentiate into stem cell-derived cancer cells (SCDCC). An amount of the SCDCC is then introduced into the patient sufficient to induce the patient's immune system to produce antibodies which inhibit or destroy the patient's cancer cells. Stem cells from multiple sources can be so co-cultured and given to the patient to enhance or otherwise improve the patient's immune response against the cancer cell.

The stems cells used in various methods of the invention can include pluripotent, multipotent or oligopotent cells. Still other forms of the stem cells are also contemplated. The SCDNICC can also be screened to remove cells having various markers and antigens such as pluripotent markers, SSEA3 and SSEA4 antigens, Tra-1-60 and antigen Tra-1-81 antigents.

Further details of these and other embodiments and aspects of the invention are described more fully below.

DESCRIPTION OF PREFERRED EMBODIMENTS

Embodiments of the invention relate to methods for using stem cells for the treatment of cancer. The stem cells used can include embryonic, fetal, and adult stem cells. Embodiments of such methods are generally applicable to the treatment of any kind of cancer, including adenocarcinoma, leukemia, lymphoma, melanoma, myeloma, sarcoma, teratocarcinoma, and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. Embodiments of these methods are also applicable for treatment of benign tumors or any disease or condition associated with the presence of abnormal cells in the body. Moreover, although treatment of humans is preferred, various embodiments of methods of the invention may also be used to treat cancers in any mammal, monkey, cow, sheep, pig, goat, mouse, rat, dog, cat, rabbit, guinea pig, hamster and horse.

In one embodiment, the present invention is directed to a method of treating cancer, the method comprising removing cancer cells from a patient, culturing the cancer cells in the presence of embryonic stem cells under conditions such that the embryonic stem cells differentiate into stem cell-derived-cancer cells (SCDCC) (i.e., a non-autologous cancer cell mimic), and introducing an amount of the SCDCC into the patient sufficient to evoke an allograft rejection response, such as inducing the patient's immune system to produce antibodies which inhibit or destroy the patient's cancer cells. The production of such antibodies along with other aspects of the allograft rejection response provide for reductions in one or more of tumor size, titer of cancer cells in the patient's body, rates of cancer cell proliferation in the patient's body and rates and/or activity levels of various metastatic processes in the patient's body. Further, one or more aspects of the methods of the invention can be adjusted to achieve particular reductions in one or more of these measurements. For example, the type and number of SCDCC introduced into the patient can be titrated for obtaining one or both of a specific reduction in the titer of cancer cells or rate of proliferation of cancers cells.

In many embodiments, the SCDCC have been screened or otherwise treated to be non-invasive SCDCC (SCDNICC). For ease of discussion, SCDCC's will be referred to as SCD-NICC's; however, it will be appreciated that in any embodiment using a stem cell derived non-invasive cancer cell, an invasive cell may also be used. Also, instead of embryonic stem cells, fetal or adult stem cells (e.g., hemopoietic stem cells) may be used; or any combination of embryonic, fetal and adult stem cells may be used.

Embryonic cells may be from any appropriate source. For example, embryonic stem cells may be grown in culture from inner cell mass cells obtained from a blastocyst. Additional examples are an embryonic stem cell line or embryonic stem cells generated through cloning. Additionally, genetically modified stem cells may also be used wherein the stem cells have been genetically modified to include genetic material for encoding one or more proteins. The genetically modified stem cells can include embryonic, fetal, or adult stem cells and combinations thereof. Genetic modification can be performed using various techniques known in the art including, for example, the use of plasmids, yeast artificial chromosomes (YAC) and bacterial artificial chromosomes (BAC) and like methods. The proteins encoded by the genetically modified stem cells can include, for example, proteins which stimulate the immune response, such as CD40, CD80, CD86, IL2, IL7, IL12, IL21, TNF, GM-CSF, etc. Still other immune stimulating proteins are contemplated. Production of proteins which stimulate the patient's immune response enhances the patient's immune response to the cancer cells and improves the efficacy of the SCDNIC in treating the patient's cancer.

The production of such immune stimulating proteins can provide for reductions in one or more of tumor size, titer of cancer cells in the patient's body, rates of cancer cell proliferation in the patient's body and rates and/or activity levels of various metastatic processes in the patient's body. Further, one or more aspects in the use of such immune stimulating proteins can be adjusted to achieve particular reductions in one or more of these measurements. For example, the type, combination and number SCDCC introduced into the patient producing a given immune stimulating protein(s) can be titrated for obtaining one or both of a specific reduction in the titer of cancer cells or rate of proliferation of cancers cells.

In some embodiments, the cancers cells can be cultured with stem cells lines from multiple mammalian sources, e.g., multiple humans, mice, etc., or from the same mammal but from different stem cell types, e.g., fetal and hemopoietic, etc. The cancer cells can be cultured with a mixture of the multiple stem cell lines or they may be cultured separately with the respective cells. In the latter case, the cultured stems lines can be delivered (e.g., by injection) as separate doses to the patient or they can be reconstituted as a mixture and delivered in a single dose or doses of the mixture. No matter what the culturing or delivery method, the use of stem cell lines from multiple sources serves to increase the likelihood of eliciting an immune response of the patient to his or her cancer due to the increased probability of producing an SCDNICC which includes one or more of the following i) an antigen sufficiently similar to an antigen on the cancer cell to produce an immune response to the cancer cell (described herein as a cancer cell antigen mimic or CCAM); ii) a CCAM of a tumorogenic antigen (CCAMTA) on the cancer cell (a tumorogenic antigen (TA) is an antigen playing a role in the tumorigenicity of the cancer cell); iii) multiple CCAMS; or iv) multiple CCAMTA's. Antibody binding to a CCAMTA can serve to both destroy the cancer cell outright (e.g., by subsequent phagocytosis by immune cells (e.g., dendritic cells and B lymphocytes) as well as inhibit the tumorigenic/invasive properties of the cancer cell. In the latter case, inhibition can be achieved by preventing the cancer cell from attaching or entering other tissue by means of the tumorigenic antigen, which is now bound by the antibody. Antigens from a particular type of cancer, including tumorogenic antigens can be identified using various immunological assays known in the art.

In particular embodiments, stem cells from two, three, four, five, ten or even more stem cell lines can be cultured with the patient's cancer cells either separately, collectively, or in groups of two or more stem cell lines. The number of stem cell lines used and method of culturing (e.g., separately or collectively, etc.) can be selected depending upon the patient and type of cancer and particular antigens present on the cancer cell line. In some embodiments, the cancer antigens can be analyzed using one or more methods known in the art (e.g. antibody screening, etc.) and this information then used to determine the appropriate stem cell line, number of stem lines and various culturing and stem cell delivery methods (e.g., singular vs. multiple doses). For example, for cancers having multiple TA's, multiple stem cell lines can be used so as to increase the probability of incorporating a given TA or TA's into the SCDNICC's as a CCAMTA. Also, particular cell lines known to have a higher likelihood for incorporation of a given TA can be selected. The number of such selective cell lines can correspond to the number of TA's or a multiple thereof.

Experiments can be performed using various immunological methods known in the art to enhance and/or optimize the number of cancer cell antigens (such as a cancer cell surface antigen) that are incorporated into the SCDNICC's. These results in turn can be used to enhance and/or optimize the patient's immune response to the cancer cells so as to kill or otherwise inhibit the patient's cancer cells.

Embryonic stem cells are typically sustained in an undifferentiated state by culture on a feeder layer of mouse embryonic fibroblasts with the inclusion of serum in the culture medium. In some embodiments, human embryonic stem cells may be maintained on a feeder layer of mouse embryonic fibroblasts with the inclusion of basis fibroblast growth factor (bFGF) in the culture medium. Mouse embryonic stem cells may be maintained on a layer of gelatin with leukemia inhibitory factor (LIF) in the culture medium. These above methods can be used for sustaining other types of stem cells such as fetal stem cells or adult stem cells (e.g., hemopoietic stem cells) and combinations thereof.

For use in the methods described herein, cancer cells from a patient are typically removed by biopsy, e.g., by a needle biopsy or other biopsy device. However, any applicable method may be used, such as removal of a whole or partial tumor or cancerous lesion via surgery, in order to obtain cancer cells from the patient. The tissue sample containing the cancer cells is dispersed through the use of proteases or other appropriate enzymes and/or mechanical dispersal. The cancers cells may also be separated and sorted from the removed tissue sample using various cell sorting methods and equipment known in the art such as flow cytometry sorting methods including FACS sorting methods.

The cancer cells are typically added to the culture medium containing the embryonic or other stem cells, although adding the stem cells to a medium containing the cancer cells is also contemplated. The density of the stem cells and cancer cells, as well as the ratio of stem cell to cancer cell, is adjusted for optimal results. Depending on the type of cancer cell, maintaining the cell co-culture under conditions used to maintain the stem cells may be adequate to induce differentiation of the stem cells into stem cell-derived non-invasive cancer cells (SCDNICC). With some cancer cells, it may be necessary to remove serum or particular growth factors (e.g., bFGF or LIF) from the culture medium before differentiation of the stem cells into SCDNICC occurs. In some cases, it may be necessary to add one or more growth factors to the culture medium to induce differentiation. These approaches can be adapted for the particular cancer cells using the methods described below.

Depending on culture conditions used to maintain the stem cells, they may be pluripotent, multipotent or oligopotent, with the type of stem cell being chosen so as to provide SCDNICC with the desired characteristics. Differentiation of stem cells into SCDNICC is typically monitored by determining the disappearance of one or more stem cell markers. For example, one can monitor the disappearance of one or more of alkaline phosphatase, alpha-fetoprotein (AFP), bone morphogenetic protein-4, brachyury, cluster designation 30

(CD30), cripto (TDGF-1), GATA-4 gene, GCTM-2, genesis, germ cell nuclear factor, hepatocyte nuclear factor-4 (HNF-4), nestin, neuronal cell-adhesion molecule (N-CAM), OCT4/POU5F1, Pax6, stage-specific embryonic antigen-3 (SSEA-3), stage-specific embryonic antigen-4 (SSEA-4), stem cell factor (SCF or c-Kit ligand), telomerase, TRA-1-60, TRA-1-81, or vimentin. If, for example, unaltered embryonic stem cells are introduced into a host then, due to the pluripotent nature of ES cells, these cells will typically differentiate into many different types of cells, causing a teratoma. Hence, it is important to insure that the SCDNICC have lost sufficient embryonic stem cell characteristics so as to not give rise to a teratoma in the patient.

As an additional, or alternate, criterion for determining when the stem cells have differentiated into SCDNICC, one can monitor whether one or more cell markers of the cancer cell have appeared on the SCDNICC. Preferably, one can monitor for the presence of one or more antigens of the cancer cell, such as one or more surface antigens. Once the SCDNICC are introduced into the patient, the patient's immune system is relied upon to mount an immune response to the SCDNICC which then also results in attack of the cancer cells in the patient. Accordingly, one or more surface or other antigens from the cancer cell should also be present on the surface of the SCDNICC so that antibodies generated in response to introduction of the SCDNICC will attack the cancer cells in the patient. Alternatively, the SCDNICC will generate a cell-based immune response which destroys the patient's cancer cells.

Furthermore, to determine whether or not the SCDNICC have unwanted characteristics of invasive cancer cells, one can monitor for antigens or markers which are associated with invasive or metastatic cancer cells. For example, breast cancer cells with $CD44^+/CD24^-$ have been reported to possess highly invasive properties. Therefore, it could be advantageous to use appropriate antibody treatment of the SCDNICC in order to remove such cells before introducing the SCDNICC back into the patient. Similar monitoring can be performed with respect to markers associated with other invasive or metastatic cancer cells. Other methods for removal of cells having antigens or markers associated with invasive or metastatic cancer cells are also contemplated (e.g., FACS scan).

In still other embodiments of the invention, one more of the above methods for improving the patient's immune response to cancers using SCDNICC cultured and introduced into the patient as described above may be combined with other forms of cancer treatment such as various other chemotherapy and radiation treatments either concurrently or in time sequence regimented fashion (e.g., a course of chemo treatment followed by SCNICC treatment). By combining therapies, additional reductions in one or more of tumor size, titer of cancer cells in the patient's body, rates of cancer cell proliferation in potential metastatic process can be achieved. This is due to the fact a proportion of cancer cells which may not respond to chemotherapy can now be targeted by the patient's own immune cells. Also many chemotherapy treatments require the patient cycle on and off of the chemotherapy treatment. Use of SCNICC treatment allows the patient's immune system to continue to reduce the number of cancer cells during an off-cycle of chemotherapy. Also delivering a SNCICC treatment during an off cycle of chemotherapy reduces any adverse effect that the course of chemotherapy may have on the SNCICC or resulting production of antibodies or other immune response. Further, should the patient's cancer cells mutate, e.g., as a result of the chemotherapy treatment, a new course of SCNICC treatment can be delivered using the mutated cancers cells to culture and introduce SCNICC as is described herein. In this way, the patient's immune system can be effectively retargeted or otherwise adjusted to any new type of cancer cell that develops.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

I claim:

1. A method for preparing stem cell-derived cancer cells, the method comprising:
   removing cancer cells from a patient;
   culturing the cancer cells in the presence of stem cells under conditions such that the stem cells differentiate into stem cell-derived cancer cells (SCDCCs) wherein the SCDCCs are stem cell derived non-invasive cancer cells (SCDNICCs); and
   monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

2. The method of claim 1, further comprising:
   exposing the SCDCC to an antibody which binds to a cell surface marker associated with an invasive cancer cell; and
   removing the antibody-bound cancer cells from the SCDNICC.

3. A method for preparing stem cell-derived cancer cells, the method comprising:
   removing cancer cells from a patient;
   culturing the cancer cells in the presence of genetically modified stem cells under conditions such that the stem cells differentiate into stem cell-derived cancer cells (SCDCCs); and
   monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

4. A method for preparing stem cell-derived cancer cells, the method comprising:
   removing cancer cells from a patient;
   culturing the cancer cells in the presence of adult hemopoietic stem cells under conditions such that the stem cells differentiate into stem cell-derived cancer cells (SCDCCs); and
   monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

5. A method for preparing stem cell-derived cancer cells, the method comprising:
removing cancer cells from a patient;
culturing the cancer cells in the presence of multipotent stem cells under conditions such that the stem cells differentiate into stem cell-derived cancer cells (SCDCCs); and
monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

6. A method for preparing stem cell-derived cancer cells, the method comprising:
removing cancer cells from a patient;
culturing the cancer cells in the presence of oligopotent stem cells under conditions such that the stem cells differentiate into stem cell-derived cancer cells (SCDCCs); and
monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

7. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a cell surface antigen SSEA3, and wherein the disappearance of the one or more stem cell markers indicates that the stem cells have differentiated into SDCCCs.

8. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a cell surface antigen SSEA4, and wherein the disappearance of the one or more stem cell markers indicates that the stem cells have differentiated into SDCCCs.

9. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a cell surface antigen Tra-1-60, and wherein the disappearance of the one or more stem cell markers indicates that the stem cells have differentiated into SDCCCs.

10. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a cell surface antigen Tra-1-81, and wherein the disappearance of the one or more stem cell markers indicates that the stem cells have differentiated into SDCCCs.

11. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a multipotent stem cell marker, and wherein the disappearance of the one or more stem cell markers indicates that the stem cells have differentiated into SDCCCs.

12. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs); and
monitoring differentiation of the stem cells by identifying the disappearance of one or more stem cell markers, wherein the one or more stem cell markers is a oligopotent stem cell marker, and wherein the disappearance of the one or more stem cell markers indicates that the stem cells have differentiated into SDCCCs.

13. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs);
monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs;
exposing the SCDCC to an antibody which binds to a cell surface marker associated with cancer metastasis; and
removing the antibody-bound cancer cells from the SCDCC.

14. A method for preparing stem cell-derived cancer cells, the method comprising:
removing cancer cells from a patient;
culturing the cancer cells in the presence of stem cells under conditions such that the stem cells differentiate into stem cell-derived cancer cells (SCDCCs), wherein the stem cells comprise a plurality of stem cell lines such that the SCDCC comprise a plurality of SCDCC lines; and
monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

15. The method of claim 14, wherein the plurality of stem cell lines comprise at least a first and second line of stem cells.

16. The method of claim 15, wherein cancer cells are cultured with both the first and second stem cell lines mixed together.

17. The method of claim 15, wherein a first group of cancer cells are cultured with the first stem cell line to produce a first group of SCDCC and a second group of cancer cells are cultured with the second stem cell line to produce a second group of SCDCC.

18. A method for preparing stem cell-derived cancer cells, the method comprising:
   removing cancer cells from a patient;
   culturing the cancer cells in the presence of stem cells under conditions such that the stem cells differentiate into stem cell-derived cancer cells (SCDCCs), wherein the stem cells have been genetically modified to produce an immune stimulating protein; and
   monitoring differentiation of the stem cells by identifying the disappearance of one or more stem cell markers and/or by identifying the appearance of one or more tumorigenic antigens, wherein the disappearance of the one or more stem cell markers and/or the appearance of the one or more tumorigenic antigens indicates that the stem cells have differentiated into SDCCCs.

19. The method of claim 18, wherein the immune stimulating protein includes CD40, CD80, CD86, IL2, IL7, IL12, IL21, TNF or GM-CSF.

* * * * *